US009037199B1

(12) United States Patent
Stogaitis et al.

(10) Patent No.: US 9,037,199 B1
(45) Date of Patent: May 19, 2015

(54) DETECTING TRANSITIONS BETWEEN PHYSICAL ACTIVITY

(71) Applicant: Google Inc., Mountain View, CA (US)

(72) Inventors: Marc Stogaitis, San Mateo, CA (US); Brian Patrick Williams, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/243,760

(22) Filed: Apr. 2, 2014

Related U.S. Application Data

(60) Provisional application No. 61/939,690, filed on Feb. 13, 2014.

(51) Int. Cl.
*H04W 52/02* (2009.01)

(52) U.S. Cl.
CPC .................. *H04W 52/0254* (2013.01)

(58) Field of Classification Search
USPC ............ 455/456.1, 456.3, 457, 574, 414.1, 455/456.6
See application file for complete search history.

(56) References Cited

U.S. PATENT DOCUMENTS

| 8,344,998 | B2 * | 1/2013 | Fitzgerald et al. ............ 345/156 |
| 8,560,004 | B1 | 10/2013 | Tsvetkov et al. |
| 2006/0161377 | A1 | 7/2006 | Rakkola et al. |
| 2007/0010940 | A1 | 1/2007 | Tan et al. |
| 2008/0234935 | A1 | 9/2008 | Wolf et al. |
| 2009/0278738 | A1 | 11/2009 | Gopinath |
| 2010/0235667 | A1 | 9/2010 | Mucignat et al. |
| 2011/0093729 | A1 | 4/2011 | Mucignat et al. |
| 2011/0312349 | A1 | 12/2011 | Forutanpour et al. |
| 2012/0254100 | A1 | 10/2012 | Grokop et al. |
| 2012/0287035 | A1 | 11/2012 | Valko et al. |
| 2012/0290252 | A1 | 11/2012 | Abraham |
| 2012/0297226 | A1 * | 11/2012 | Mucignat et al. ............. 713/323 |
| 2014/0028477 | A1 * | 1/2014 | Michalske .................... 340/990 |

FOREIGN PATENT DOCUMENTS

WO    2014/035119 A2    3/2014

OTHER PUBLICATIONS

Beckler, "Accelerometer-Based Intertial Navigation," University of Minnesota Electrical and Computer Engineering Department, May 9, 2008, 17 pp.
Cochibo, "Arrow knows where you parked—Arrow Car Finder," Cochibo, Novemer 15, 2012, retrieved from <http://cochibo.com/arrow/>, 4 pp.

(Continued)

*Primary Examiner* — Blane J Jackson
(74) *Attorney, Agent, or Firm* — Shumaker & Sieffert, P.A.

(57) ABSTRACT

In one example, a method includes determining, by a processor operating in a first power mode and based on first motion data, a first activity of a user, transitioning from operating in the first power mode to operating in a second power mode, wherein the processor consumes less power while operating in the second power mode than in the first power mode, responsive to determining, while the processor is operating in the second power mode and based on second motion data, that a change in an angle relative to gravity satisfies a threshold, transitioning from operating in the second power mode to operating in the first power mode, determining, by the processor and based on second motion data, a second activity of the user, and, responsive to determining that the second activity is different from the first activity, performing an action.

21 Claims, 5 Drawing Sheets

(56) References Cited

OTHER PUBLICATIONS

Cochibo, "Arrow knows where you parked—FAQ," Cochibo, Nov. 15, 2012, retrieved from <http://cochibo.com/ arrow/faq/>, 2 pp.

jophde, "Valet," Google Play, Apr. 3, 2014, retrieved from <https://play.google.com/store/apps/details?id=co.valetapp>, 3 pp.

Mathie, "Monitoring and Interpreting Human Movement Patterns Using a Triaxial Accelerometer," The University of New South Wales—Faculty of Engineering, Aug. 2003, 512 pp.

Data Sheet "BMA 220 Digital, triaxial acceleration sensor," Bosch Sensortec, Document revision 1.15, Document release date Aug. 23, 2011, downloaded from http://ae-bst.resource.bosch.com/media/productsdokumente/bma220/bst-bma220-ds003-08.pdf, 63 pp.

Keyboadr, "Auto-Finder—Android Apps on Google Play," Feb. 24, 2014, retrieved from <http://play.google.com/store/apps/details?id=com.keyboardr.parkingwithglass> 3 pp.

U.S. Appl. No. 14/230,880, filed Mar. 31, 2014, by Le Grand et al.

Khan et al., "A Triaxial Accelerometer-Based Physical-Activity Recognition view Augmented-Signal Features and a Hierarchical Recognizer," IEEE Transactions on Information Technology in Biomedicine, vol. 14, No. 5, Sep. 2010, pp. 1166-1172.

Subramanya et al., "Recognizing Activities and Spatial Context Using Wearable Sensors," Proc. of Conference on Uncertainty in AI (UAI), 2006, 10 pp.

Khan, "Human Activity Recognition Using a Single Tri-axial Accelerometer," Kyung Hee University—Department of Computer Engineering, Feb. 2011, 160 pp.

Khan et al., "A Feature Extraction Method for Realtime Human Activity Recognition on Cell Phones," Proc of International Symposium on Quality of Life Technology, 2011, 6 pp.

Lee et al., "Activity and Location Recognition Using Wearable Sensors," Pervasive Computing, 2002, 9 pp.

Mannini et al., "Machine Learning Methods for Classifying Human Physical Activity from On-Body Accelerometers," MDPI—Open Access Sensors, Feb. 1, 2010, 22 pp.

Abbott et al., "Land-Vehicle Navigation Using GPS," Proceedings of the IEEE, vol. 87, No. 1, Jan. 1999, 18 pp.

Weston et al., "Modern inertial navigation technology and its application," Electronics & Communication Engineering Journal, Apr. 2000, 16 pp.

\* cited by examiner

DETECTING TRANSITIONS BETWEEN PHYSICAL ACTIVITY

This application claims the benefit of U.S. Provisional Application No. 61/939,690, filed Feb. 13, 2014, the entire content of which is hereby incorporated by reference.

BACKGROUND

Mobile computing devices provide the benefit of being portable while allowing a user to perform a variety of functions including various forms of communication and computing. For example, some mobile devices are capable of accessing the Internet, executing gaming applications, playing videos and music, as well as providing functionality of a traditional mobile, e.g. cellular, phone. Such devices are generally powered by a rechargeable battery. A persistent challenge in mobile device design is increasing the length of time the device may operate without recharging the battery.

Some computing devices may include one or more accelerometers to detect device movements. To conserve power, some computing devices only collect accelerometer data for a few seconds and at periodic intervals, such as every five minutes. In some instances, the computing device may analyze the collected accelerometer data to determine which physical activity a user may be currently be engaged. However, while limiting the accelerometer data collected by the computing device may increase battery life, the computing device may move in a meaningful way during the time between the data collection periods, which may reduce the accuracy of the physical activity determinations and which may result in activity transitions being missed by the mobile device.

SUMMARY

In one example, a method includes determining, by a processor of a mobile computing device operating in a first power mode and based on first motion data generated by a motion sensor of the mobile computing device, a first activity of a user associated with the mobile computing device, the first motion data indicating movement of the mobile computing device during a first time period, and transitioning, by processor, from operating in the first power mode to operating in a second power mode, wherein the processor consumes less power while operating in the second power mode than while operating in the first power mode. The method may further include, while the processor is operating in the second power mode, determining, by a motion module of the mobile computing device and based on second motion data generated by the motion sensor, that a change in an angle of the mobile computing device relative to gravity satisfies a threshold amount of change, and, responsive to determining that the change in the angle satisfies the threshold amount of change, transitioning, by processor, from operating in the second power mode to operating in the first power mode. The method may further include determining, by the processor and based on second motion data generated by the motion sensor during a second time period, a second activity of the user of the mobile computing device, and, responsive to determining that the second activity is different from the first activity, performing, by the mobile computing device, an action determined based on the determining that the second activity is different from the first activity.

In another example, a computing device includes one or more processors, a motion sensor, and a motion module. At least one processor of the one or more processors determines, while the at least one processor is operating in a first power mode and based on first motion data generated by the motion sensor, a first activity of a user associated with the mobile computing device, the first motion data indicating movement of the mobile computing device during a first time period, and transitions the mobile computing device from operating in the first power mode to operating in a second power mode, wherein the one or more processors consume less power while operating in the second power mode than while operating in the first power mode. The motion module determines, while the mobile computing device is operating in the second power mode and based on second motion data generated by the motion sensor, that a change in an angle of the mobile computing device relative to gravity satisfies a threshold amount of change, and the at least one processor of the one or more processors, responsive to the motion module determining that the change in the angle satisfies the threshold amount of change, transitions the mobile computing device from operating in the second power mode to operating in the first power mode, determines, based on second motion data generated by the motion sensor during a second time period, a second activity of the user of the mobile computing device, and, responsive to determining that the second activity is different from the first activity, performs an action determined based on the determining that the second activity is different from the first activity.

In another example, a non-transitory computer-readable storage medium encoded with instructions that, when executed, cause at least one processor of a plurality of processors of a mobile computing device to determine, while the at least one processor is operating in a first power mode and based on first motion data generated by a motion sensor of the mobile computing device, a first activity of a user associated with the mobile computing device, the first motion data indicating movement of the mobile computing device during a first time period, and transition, by the at least one processor, from operating in the first power mode to operating in a second power mode, wherein the at least one processor consumes less power while operating in the second power mode than while operating in the first power mode. The instructions further cause the at least one processor to, while the at least one processor is operating in the second power mode, determine, by a motion module and based on second motion data generated by the motion sensor, that a change in an angle of the mobile computing device relative to gravity satisfies a threshold amount of change, responsive to determining that the change in the angle satisfies the threshold amount of change, transition, by the at least one processor, from operating in the second power mode to operating in the first power mode, determine, based on second motion data generated by the motion sensor during a second time period, a second activity of the user of the mobile computing device, and, responsive to determining that the second activity is different from the first activity, perform an action determined based on the determining that the second activity is different from the first activity.

The details of one or more examples of the disclosure are set forth in the accompanying drawings and the description below. Other features, objects, and advantages will be apparent from the description and drawings, and from the claims.

DETAILED DESCRIPTION

Figure 1:
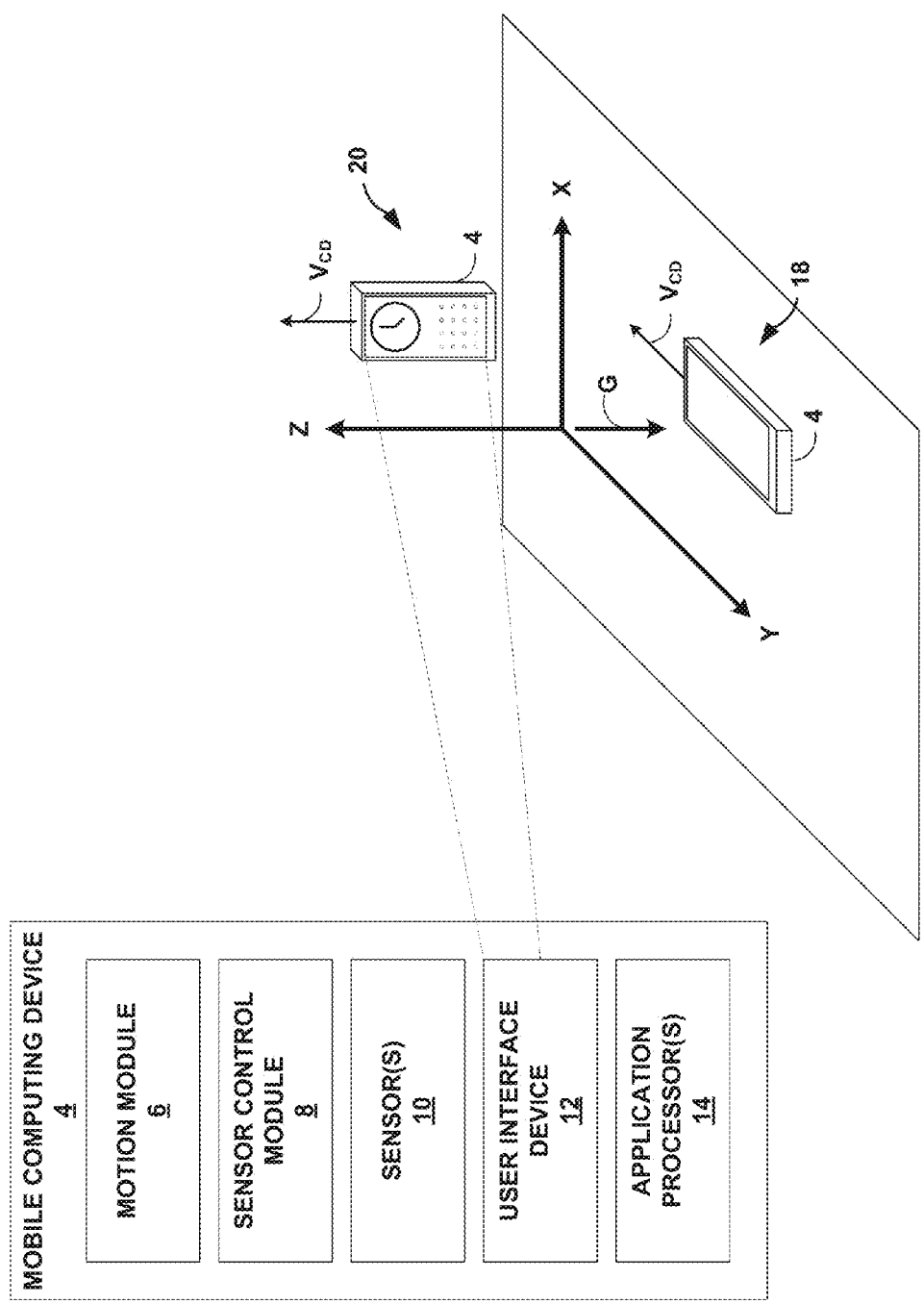
FIG. 1 is a block diagram illustrating an example computing device that is configured to detect activity transitions, in accordance with one or more techniques of the present disclosure.

In general, techniques of the disclosure are directed to a computing device that detects, based on a change in tilt of the computing device relative to gravity, transitions between different physical activities in which a user associated with the computing device may currently be engaged. For instance, the computing device may be stored in a pocket of a user while the user is sitting at desk. Responsive to a motion module of the computing device determining that the angle of the computing device relative to gravity (i.e., the tilt of the computing device) has changed by at least a threshold amount, the motion module of the computing device may cause a processor of the computing device to transition from operating in a low-power mode to operating in a higher-power mode. The processor may analyze motion data generated by a motion sensor of the computing device over a period of time and determine an activity in which the user is currently engaged. The processor may determine whether the user has transitioned between activities by, for example, comparing the determined current activity to an activity in which the user was engaged as determined by the computing device prior to detection of the tilt event. Moreover, the tilt event may trigger the computing device to transition from operating in a lower power mode to operating in a higher-power mode, and may cause the computing device to determine, while operating in the high power mode, whether the user has transitioned to a new activity.

Continuously collecting and analyzing motion data to determining transitions between physical activities associated with a user may use a significant quantity of power (e.g., power stored in a battery of a computing device). Therefore, rather than continuously collecting and analyzing such data, techniques of the disclosure may be used to activate the processor responsive to a preliminary determination of a change in the angle of the computing device by the lower power consuming motion module. Moreover, collection and processing of motion data for determination of whether the angle of the computing device has changed at least a threshold amount may be accomplished with lower power consumption and, as such, may be applied even though the computing device is in a lower-power mode. In this way, as opposed to operating relatively higher power-consuming devices, the computing device may activate the processor and transition the processor to a high-power mode for further, finer-grain motion data collection and analysis, based on an initial determination by the lower power-consuming motion module. Moreover, while in low-power mode, the motion module may continuously monitor the angle of the computing device without collecting and analyzing full motion data for the mobile computing device, and may activate the processor and the activity determination process with lower latency than activating the processor and the activity determination process at an arbitrary or periodic interval. As such, the techniques may enable faster response time and, therefore, faster detection of changes in the activity of the user.

FIG. 1 is a block diagram illustrating an example mobile computing device that is configured to detect activity transitions, in accordance with one or more techniques of the present disclosure. As shown in the example of FIG. 1, mobile computing device 4 may include motion module 6, sensor control module 8 ("SCM 8"), one or more sensors 10, user interface device 12 ("UID 12"), and one or more application processors 14.

Mobile computing device 4 may include any number of different portable electronic computing devices, including, e.g., cellular phones, personal digital assistants (PDAs), laptop computers, portable gaming devices, portable media players, e-book readers, watches. Mobile computing device 4 may include various input and output components, including, e.g. one or more processors, memory, telemetry modules, cellular network antennas, a display, one or more UI elements, sensors, and a power source like a rechargeable battery. Further details of mobile computing device 4 are described in FIG. 2. Other examples of mobile computing device 4 that implement techniques of this disclosure may include additional components not shown in FIG. 1.

In some examples, mobile computing device 4 may include motion module 6. Motion module 6 may collect and analyze motion data corresponding to the movement of mobile computing device 4. For instance, motion module 6 may determine whether or not mobile computing device 4 has moved. In some examples, motion module 6 may determine whether or not mobile computing device 4 has moved by analyzing motion data received from a motion sensor included in motion module 6. In other words and as further illustrated in FIG. 2, motion module 6 may include a motion sensor to measure motion data (e.g., a motion sensor of sensors 10) and a processor to analyze the measured motion data. In some examples, motion module 6 may be a low power device. For instance, motion module 6 may use less power than sensor control module 8 and/or application processors 14. As one example, in operation, motion module 6 may use approximately 0.1 milliwatts (mW). In another example, motion module 6 may use power in a range of 0.01-3.0 mW. In some examples, motion module 6 may output a signal to one or more other components of mobile computing device 4 in response to determining that mobile computing device 4 has moved (e.g., that an angle of mobile computing device 4 relative to gravity has changed at least a threshold amount). For instance, motion module 6 may output an interrupt signal to SCM 8 in response to determining that mobile computing device 4 has moved.

In some examples, mobile computing device 4 may include SCM 8. SCM 8 may communicate with one or more of sensors 10 and/or motion module 6. In some examples, SCM 8 may be referred to as a "sensor hub" that operates as an input/output controller for one or more of sensors 10 and/or motion module 6. For example, SCM 8 may exchange data with one or more of sensors 10 and/or motion module 6, such as motion data corresponding to mobile computing device 4. In some examples, SCM 8 may control the power state of one or more of sensors 10. For instance, SCM 8 may switch one or more of sensors 10 between an on power state and an off power state where more power is consumed by the one or more sensors 10 in the on power state than in the off power state. In this way, SCM 8 may control the amount of power consumed by one or more of sensors 10. SCM 8 may also communicate with application processors 14. In some examples, SCM 8 may use more power than motion module 6 but less power than application processors 14. As one example, in operation, SCM 8 may use power in a range of 20-200 mW.

SCM 8 may analyze data received from motion module 6 and/or one or more of sensors 10. SCM 8 may determine that a change in an angle of mobile computing device 4 relative to gravity satisfies a threshold amount of change based on motion data measured by one or more of sensors 10. That is, SCM 8 may determine a statistic based on the motion data. If the statistic satisfies a threshold, SCM 8 may determine that the tilt of mobile computing device 4 indicates a possible transition in a current activity of the user. Responsive to determining that the change in the angle of mobile computing device 4 relative to gravity satisfies a threshold amount of, SCM 8 may cause application processors 14 to transition from a low power state to a relatively higher power state.

In some examples, SCM 8 may receive one or more interrupt signals, for example, from motion module 6. In response to receiving an interrupt signal, SCM 8 may cause applications processors 14 to transition from a low-power or "sleep" state into one or more higher power states. Application processors 14 may consume less power in the low-power state than in the higher power states.

In some examples, mobile computing device 4 may include one or more sensors 10. One or more of sensors 10 may measure one more measurands. Examples of one or more of sensors 10 may include an accelerometer, a gyroscope, a light sensor, a temperature sensor, a pressure (or grip) sensor, a physical switch, a proximity sensor, or a button.

In some examples, mobile computing device 4 may include UID 12. A user associated with mobile computing device 4 may interact with mobile computing device 4 by providing various user inputs into mobile computing device 4, e.g., using the at least one UID 12. In some examples, UID 12 may receive tactile, audio, or visual input. In addition to receiving input from a user, UID 12 may output content, such as a graphical user interface (GUI) for display. In some examples, UID 12 can include a display and/or a presence-sensitive input device. In some examples, the presence-sensitive input device and the display may be integrated into a presence-sensitive display, which displays the GUI and receives input from the user using capacitive, inductive, surface acoustic wave, and/or optical detection at or near the presence sensitive display. That is, UID 12, in some examples may be a presence-sensitive display. In other examples, the display device can be physically separate from a presence-sensitive device included in mobile computing device 4.

In some examples, mobile computing device 4 may include one or more application processors 14. One or more application processors 14 may implement functionality and/or execute instructions within mobile computing device 4. These instructions executed by application processors 14 may cause mobile computing device 4 to read/write/etc. information during program execution. Examples of one or more of application processors 14 may include one or more microprocessors, digital signal processors (DSPs), application specific integrated circuits (ASICs), field programmable gate arrays (FPGAs), or any other equivalent integrated or discrete logic circuitry, as well as any combinations of such components.

The example of FIG. 1 illustrates a frame of reference in which the orientation of mobile computing device 4 may be identified by relative terms, such as vertical and horizontal. In some examples according to this disclosure, the frame of reference in which a motion sensor determines the orientation of a computing device may differ from that shown in FIG. 1. However, the examples described below include motion sensors that determine orientations in a frame of reference in accordance with the example of FIG. 1. Thus, "vertical" and "horizontal" in such examples correspond to orientations that are treated as generally parallel to gravity and perpendicular to the ground and generally perpendicular to gravity and parallel to the ground, respectively. However, in practice, the orientation of mobile computing device 4 may not be exactly or nearly exactly vertical or horizontal as represented by vector, $V_{CD}$, in orientations 18 and 20 in FIG. 1. Thus, FIG. 1 and the associated description provided below illustrate how the orientation of a computing device may be determined with one or more motion sensors when the computing device is only approximately vertical or horizontal, e.g. as defined in the example of FIG. 1, by employing a range of orientations within which the computing device's orientation vector as determined by the motion sensor may lie to designate the computing device in a particular orientation.

Rather than configuring applications processors 14 to periodically transition to a higher-power mode to collect and analyze motion data generated by sensors 10 to determine a current activity of a user of mobile computing device 4, techniques of this disclosure may enable mobile computing device 4 to continuously monitor an angle of mobile computing device 4 using motion module 6 and cause applications processors to transition to the higher-power mode and execute the activity determination process in response to determining that the change in the angle of mobile computing device 4 relative to gravity satisfies a threshold amount of change (e.g., a change of 15 degrees, 20 degrees, 25 degrees, 30 degrees, 35 degrees, 40 degrees, etc. in the angle of mobile computing device 4 relative to gravity). For instance, mobile computing device 4 may determine that the user is likely transitioning between activities in response to motion data indicating that the user has picked-up mobile computing device 4, stood up, sat down, or otherwise caused the angle (e.g., the tilt) of mobile computing device 4 to change a threshold amount.

At a first time, mobile computing device 4 may be in a first orientation. As illustrated by FIG. 1, mobile computing device 4 may be in first orientation 18 in which mobile computing device 4 may be horizontal (e.g., located in a user's pocket while the user is sitting down). For instance, in first orientation 18, $V_{CD}$ may be perpendicular to gravity vector G, and UID 12 may be facing up. In some examples, first orientation 18 may be different than as illustrated in FIG. 1. For instance, UID 12 may be facing down. Additionally, at the first time, mobile computing device 4 may be in a low-power state in which one or more components of mobile computing device 4 may be off, deactivated, sleeping, have limited functionality, etc. For instance, at the first time, UID 12 may be deactivated, one or more of sensors 10 may be off, and SCM 8 and application processors 14 may be sleeping. In this way, mobile computing device 4 may consume a reduced amount of power in the low-power state when compared to a normal operating state.

In any case, a user may change the angle of mobile computing device 4 by, for example, standing up. For instance, when mobile computing device 4 is stored in a pocket of the user, the user may move mobile computing device 4 from a first (e.g., orientation 18) to a second orientation (e.g., orientation 20) by standing up. Motion module 6 may determine, based on motion data measured by a motion sensor of sensors 10, that the angle of mobile computing device 4 relative to gravity has changed. In other words, motion module 6 may determine that mobile computing device 4 has moved in response to simple motion. In response to determining that mobile computing device 4 has moved from the first orientation to the second orientation, motion module 6 may output a signal (e.g., an interrupt signal) to SCM 8 or application processors 14.

Responsive to receiving the signal from motion module 6, SCM 8 and/or application processors 14 may transition from a low-power state to a higher-power state. In other words, after receiving the signal from motion module 6, SCM 8 and/or application processors 14 may begin to consume power at a higher rate than before receiving the signal.

Application processors 14 may determine whether a user of mobile computing device 4 is transitioning between activities. Responsive to transitioning to the higher-power state, application processors 14 may receive motion data for a period of time. In some examples, the period of time may be one second, three seconds, ten seconds, etc. The motion data may be generated by one or more of sensors 10 (e.g., an accelerometer) during the time period. Application processors 14 may analyze the motion data to determine a current activity of the user. For instance, the motion data may indicate that the user is walking, bicycling, sitting, riding in a vehicle, etc.

Application processors 14 may determine the current activity in many different ways. As one example, application processors 14 may analyze a series of data points generated by motion module 6. Motion module 6 may generate the data points over a single period of time (e.g., a three second period) or over two or more noncontiguous periods of time. In general, the data points correspond to motion of mobile computing device 4. The activity determination process may compare the pattern of movement indicated by the data points to one or more template patterns for each different type of activity. That is, in determining the activity, application processors 14 may classify the series of data points as being associated with the particular activity.

Application processors 14 may compare the determined current activity of the user to a previously determined activity of the user (e.g., determined prior to motion module 6 determining that a change in the angle of mobile computing device 4 satisfied a threshold amount of change). If application processors 14 determine that the current activity is different than the previously determined activity, application processors 14 may cause mobile computing device 4 to perform an action. For example, mobile computing device 4 may determine a current location of mobile computing device 4 (e.g., using one of sensors 10, such as a global positioning system sensor), may determine a current time, may output an indication of the previously determined activity and/or the current activity, may determine an amount of time that has elapsed since application processors 14 initially determined the previously determined activity, etc.

In some examples, mobile computing device 4 may be configured to periodically determine a current activity of the user, regardless of any potential change in the angle of mobile computing device 4. In these examples, techniques of this disclosure may enable improved activity classifications. That is, techniques of this disclosure may enable mobile computing device 4 to be configured such that changes in the angle of mobile computing device 4 sufficient to satisfy the threshold may be used to mark the start and end of a particular user activity.

If the activity detection process results in misclassification of the current activity, techniques of this disclosure may enable mobile computing device 4 to perform error checking and correction. For example, if the activity detection process determines, at a first time, that the change in the angle of mobile computing device 4 satisfies the threshold amount of change, responsive to the change in the angle, determines that a user is bicycling, at a next period determines that the user is walking, at a next period, determines that the user is bicycling, and then determines that a change in the angle of mobile computing device 4 satisfies the threshold amount of change, mobile computing device 4 may be configured to determine that the walking activity determination is an error (i.e., incorrect). In this manner, techniques of this disclosure may improve the accuracy of the activity recognition process by either rejecting outliers or at least performing additional activity classification when activity transitions occurred without a corresponding tilt detection.

That is, mobile computing device 4 may, prior to determining the first activity of the user, determine, based on motion data generated by the motion sensor, that a first change in an angle of the mobile computing device relative to gravity satisfies the threshold amount of change. Application processors 14 may determine a plurality of previously determined activities, wherein each previously determined activity was determined during a time period occurring between the determining that the first change in an angle of the mobile computing device relative to gravity satisfies the threshold amount of change and determining that the second change in an angle of the mobile computing device relative to gravity satisfies the threshold amount of change. Responsive to determining that at least one previously determined activity from the plurality of previously determined activities is incorrect, application processors 14 may correct the at least one previously determined activity. In some instances, applications processors 14 may correct the at least one previously determined activity by removing the at least one previously determined activity from the plurality of previously determined activity and/or by changing the at least one previously determined activity to correspond to an activity of a majority of the plurality of previously determined activities.

In various instances, mobile computing device 4 may be configured to include tilt detection into an activity transition model, such as a hidden Markov model. For instance, the activity transition model may include the probability of a user going from being in a car to being on a bicycle versus being on foot and the probabilities of determining a particular activity based on a previously determined activity. For example, mobile computing device 4 may be configured with a high probability of a user going from on foot to entering a vehicle and to being in a vehicle to exiting a vehicle, while having a low probability of doing directly from being in the vehicle to being on a bicycle. We would then assign a high probability to detecting a tilt (i.e., a change in the angle of mobile computing device 4 that satisfies the threshold amount of change) when mobile computing device 4 determines that the user is entering or exiting a vehicle.

In some examples, rather than motion module 6 causing application processors 14 to transition from operating in a low power state to operating in a higher power state, application processors 14 may be configured to periodically collect motion data and determine whether the angle of mobile computing device 4 relative to gravity has changed a threshold amount as compared to a previously calculated angle of mobile computing device 4 relative to gravity. Typically, application processors 14 determining a current angle of mobile computing device 4 relative to gravity requires less power and analysis of less motion data (e.g., fewer accelerometer data points) than when application processors 14 determine a current activity of the user. Accordingly, mobile computing device 4 may be configured to determine if the angle of mobile computing device 4 has changed by a threshold amount more frequently than it may be configured to determine a current activity of the user without increasing power consumption. In this manner, techniques of this disclosure may enable examples of mobile computing device 4 that do not include motion module 6 to reduce the latency of detecting activity transitions.

Figure 2:
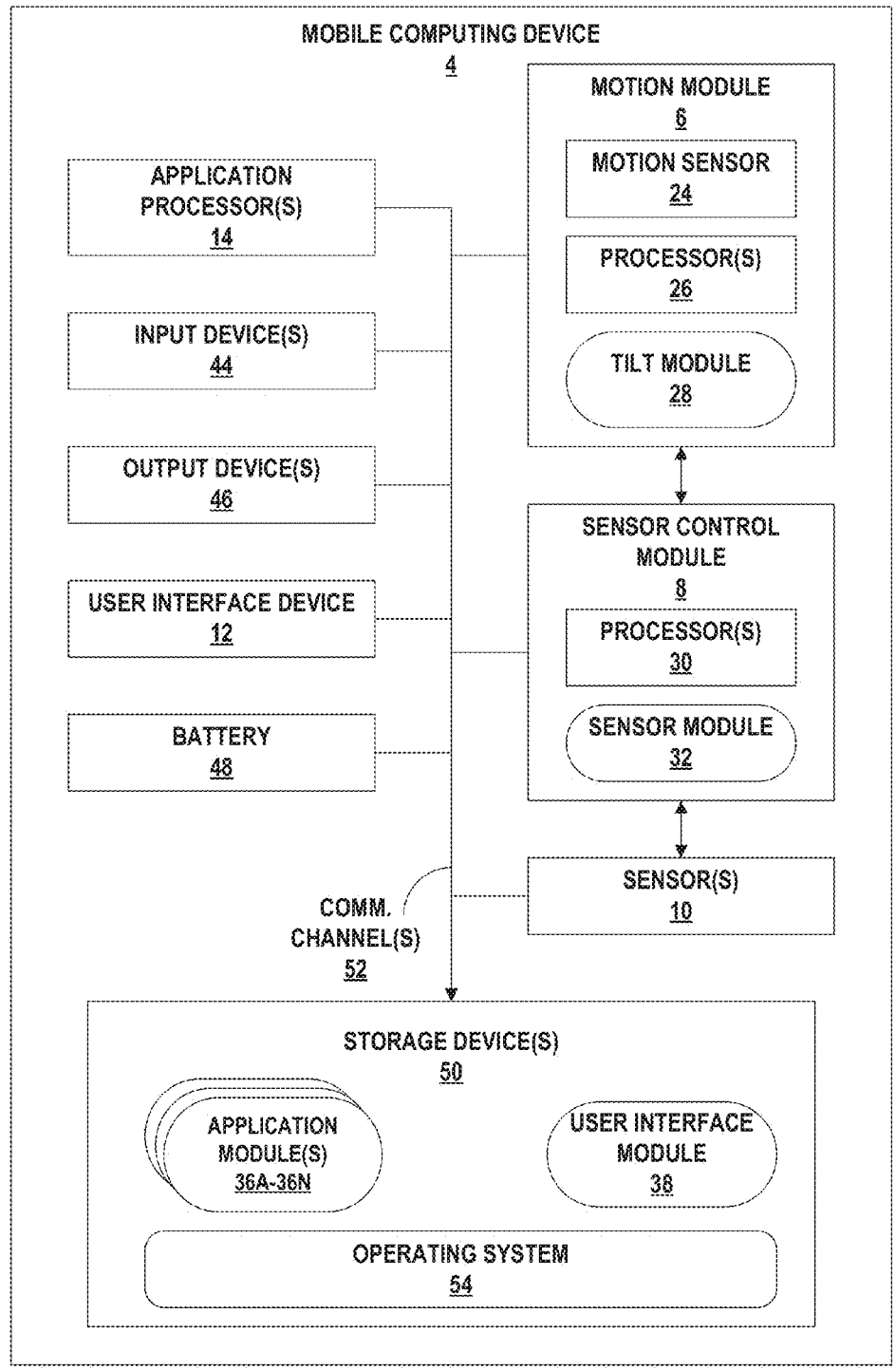
FIG. 2 is a block diagram illustrating an example computing device, in accordance with one or more techniques of the present disclosure.

FIG. 2 is a block diagram illustrating an example computing device, in accordance with one or more techniques of the present disclosure. FIG. 2 illustrates one particular example of mobile computing device 4, and many other examples of mobile computing device 4 may be used in other instances and may include a subset of the components included in example mobile computing device 4 or may include additional components not shown in FIG. 2.

As shown in the example of FIG. 2, mobile computing device 4 includes motion module 6, sensor control module 8 ("SCM 8"), one or more sensors 10, user interface device 12 ("UID 12"), one or more application processors 14, one or more input devices 44, one or more output devices 46, battery 48, and one or more storage devices 50. Storage devices 50 of mobile computing device 4 may also include application modules 36A-36N (collectively, "application modules 36"), user interface module 38 ("UIM 38") and operating system 54. Mobile computing device 4 can include additional components that, for clarity, are not shown in FIG. 2. For example, mobile computing device 4 can include a communication unit to enable mobile computing device 4 to communicate with other devices. Similarly, the components of mobile computing device 4 shown in FIG. 2 may not be necessary in every example of mobile computing device 4. For example, in some configurations, mobile computing device 4 may not include output devices 46.

Communication channels 52 may interconnect each of the components 6, 8, 10, 12, 14, 44, 46, 48, and 50 for inter-component communications (physically, communicatively, and/or operatively). In some examples, communication channels 52 may include a system bus, a network connection, an inter-process communication data structure, or any other method and/or structure for communicating data.

One or more application processors 14 may implement functionality and/or execute instructions within mobile computing device 4. For example, application processors 14 on mobile computing device 4 may receive and execute instructions stored by storage devices 50 that execute the functionality of modules 36, 38, and 54. These instructions executed by application processors 14 may cause mobile computing device 4 to read/write/etc. information, such as one or more data files stored within storage devices 50 during program execution. Application processors 14 may execute instructions of modules 36, 38, and 50 to cause UID 12 to output one or more graphical indications of incoming communications for display at UID 12 as content of a user interface. That is, application modules 36, UIM 38, and 54 may be operable by application processors 14 to perform various actions or functions of mobile computing device 4, for instance, causing UID 12 to a present a graphical user interface at UID 12.

One or more input devices 44 of mobile computing device 4 may receive input. Examples of input are tactile, audio, and video input. One or more of input devices 44 of mobile computing device 4, in one example, may include a presence-sensitive display, touch-sensitive screen, mouse, keyboard, voice responsive system, video camera, microphone, or any other type of device for detecting input from a human or machine.

One or more output devices 46 of mobile computing device 4 may generate output. Examples of output are tactile, audio, and video output. One or more of output devices 46 of mobile computing device 4, in one example, may include a presence-sensitive display, sound card, video graphics adapter card, speaker, cathode ray tube (CRT) monitor, liquid crystal display (LCD), or any other type of device for generating output to a human or machine.

In some examples, UID 12 of mobile computing device 4 may include functionality of input devices 44 and/or output devices 46. In the example of FIG. 2, UID 12 may be a presence-sensitive display. In some examples, a presence-sensitive display may include a presence sensitive input device that detects an object at and/or near a screen. As one example range, a presence-sensitive input device may detect an object, such as a finger or stylus that is within two inches or less of the screen. The presence-sensitive input device may determine a location (e.g., an (x,y) coordinate) of a screen at which the object was detected. In another example range, a presence-sensitive input device may detect an object six inches or less from the screen and other ranges are also possible. The presence-sensitive input device may determine the location of the screen selected by a user's finger using capacitive, inductive, and/or optical recognition techniques. In some examples, presence sensitive display also includes an output device that provides output to a user using tactile, audio, or video stimuli (e.g., the output device may be a display device) as described with respect to output device 46, e.g., at a display. In the example of FIG. 2, UID 12 may present one or more graphical user interfaces.

While illustrated as an internal component of mobile computing device 4, UID 12 also represents an external component that shares a data path with mobile computing device 4 for transmitting and/or receiving input and output. For instance, in one example, UID 12 represents a built-in component of mobile computing device 4 located within and physically connected to the external packaging of mobile computing device 4 (e.g., a screen on a mobile phone). In another example, UID 12 represents an external component of mobile computing device 4 located outside and physically separated from the packaging of mobile computing device 4 (e.g., a monitor, a projector, etc. that shares a wired and/or wireless data path with a tablet computer).

Motion module 6 may collect and analyze motion data corresponding to the movement of mobile computing device 4. For instance, motion module 6 may determine whether or not mobile computing device 4 has moved. As illustrated in FIG. 2, motion module 6 may include motion sensor 24, one or more processors 26, and tilt module 28. In some examples, motion module 6 may be a discrete component within mobile computing device 4. In some examples, motion module 6 may be integrated into one or more other components of mobile computing device 4, such as sensor control module 8. In some examples, motion module 6 may include additional components that, for simplicity, are not shown in FIG. 2. For instance, motion module 6 may include one or more analog-to-digital converters which may facilitate communication between motion sensor 24 and one or more of processors 26. Additionally, motion module 6 may include one or more storage devices which may store tilt module 28.

Motion sensor 24 may measure motion information associated with mobile computing device 4. For instance, motion sensor 24 may measure the rotation, velocity, and/or acceleration of mobile computing device 4. Examples of one or more of motion sensor 24 may include an accelerometer, a gyroscope, or any other device capable of measuring the rotation, velocity, and/or acceleration of mobile computing device 4. Motion sensor 24 may output measured motion data to one or more components of mobile computing device 4, such as one or more of processors 26 and/or SCM 8.

Processors 26 may implement functionality and/or execute instructions within motion module 6. For example, one or more of processors 26 may receive and execute instructions stored by a storage device that execute the functionality of tilt module 28. These instructions executed by one or more of processors 26 may cause motion module 6 to read/write/etc. information, such as one or more data files stored within a storage device during program execution. Examples of one or more of processors 26 may include one or more microprocessors, digital signal processors (DSPs), application specific integrated circuits (ASICs), field programmable gate arrays (FPGAs), or any other equivalent integrated or discrete logic circuitry, as well as any combinations of such components.

Tilt module 28 may be executable by one or more of processors 26 to analyze motion data measured by motion sensor 24. For instance, tilt module 28 may determine that a change in an angle of mobile computing device 4 relative to gravity satisfies a threshold amount of change based on motion data measured by motion sensor 24. That is tilt module 28 may determine when the change in the angle of mobile computing device 4 is sufficient to be classified as a tilt event. Tilt module 28 may output a signal to one or more other components of mobile computing device 4 in response to determining that mobile computing device 4 has tilted. For instance, tilt module 28 may output an interrupt signal to SCM 8 in response to determining that mobile computing device 4 has tilted.

SCM 8 may collect and analyze sensor data. For instance, SCM 8 may collect any analyze sensor data from one or more of sensors 10 and/or motion sensor 24. As illustrated in FIG. 2, SCM 8 may include one or more processors 30, and sensor module 32. In some examples, SCM 8 may be a discrete component within mobile computing device 4. In some examples, SCM 8 may be integrated into one or more other components of mobile computing device 4, such as one or more of application processors 14. In some examples, SCM 8 may include additional components that, for simplicity, are not shown in FIG. 2. For instance, SCM 8 may include one or more analog-to-digital converters which may facilitate communication between one or more of sensors 10 and one or more of processors 30. Additionally, SCM 8 may include one or more storage devices which may store sensor module 32.

Processors 30 may implement functionality and/or execute instructions within SCM 8. For example, one or more of processors 30 may receive and execute instructions stored by a storage device that execute the functionality of sensor module 32. These instructions executed by one or more of processors 30 may cause SCM 8 to read/write/etc. information, such as one or more data files stored within a storage device during program execution.

SCM 8 may receive one or more interrupt signals. In response to receiving an interrupt signal, SCM 8 may transition from a low-power or "sleep" state into one or more higher power states. SCM 8 may consume less power in the low-power state than in the higher power states. For instance, SCM 8 may consume 0.1 mW of power in the low-power state, and between 20 mW and 200 mW of power in the higher power states. In some examples, in response to receiving an interrupt signal, one or more of processors 30 may execute sensor module 32.

Sensor module 32 may be executable by one or more of processors 30 to analyze sensor data measured by one or more of sensors 10 and/or motion sensor 24. For instance, sensor module 32 may determine one or more statistics based on sensor data measured by one or more of sensors 10 and/or motion sensor 24. If at least one of the statistics satisfies a threshold, sensor module 32 may determine that mobile computing device 4 has tilted (i.e., the change in the angle of mobile computing device 4 satisfies a threshold amount of change). Sensor module 32 may output a signal to one or more other components of mobile computing device 4 (e.g., in response to determining that mobile computing device 4 has tiled). For instance, sensor module 32 may output a signal to one or more components of mobile computing device 4 that causes one or more application processors to perform a user activity determination process.

Sensors 10 may collect information associated with mobile computing device 4. For instance, one or more of sensors 10 may measure the geographical location, object clearance, rotation, velocity, and/or acceleration of mobile computing device 4. Examples of one or more of sensors 10 may include an accelerometer, a gyroscope, a global positioning system sensor, a light sensor, a temperature sensor, a pressure (or grip) sensor, a physical switch, a proximity sensor, or a button. In some examples, one or more of sensors 10 may include one or more processors. For instance, one or more of sensors 10 may include one or more microprocessors, digital signal processors (DSPs), application specific integrated circuits (ASICs), field programmable gate arrays (FPGAs), or any other equivalent integrated or discrete logic circuitry, as well as any combinations of such components.

One or more storage devices 50 within mobile computing device 4 may store information for processing during operation of mobile computing device 4 (e.g., mobile computing device 4 may store data that modules 36 and 38 and operating system 54 may access during execution at mobile computing device 4). In some examples, storage device 50 is a temporary memory, meaning that a primary purpose of storage device 50 is not long-term storage. Storage devices 50 on mobile computing device 4 may configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage devices 50, in some examples, also include one or more computer-readable storage media. Storage devices 50 may store larger amounts of information than volatile memory. Storage devices 50 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage devices 50 may store program instructions and/or information (e.g., data) associated with application modules 36, UIM 38, and operating system 54.

Operating system 54, in some examples, controls the operation of components of mobile computing device 4. For example, operating system 54, in one example, facilitates the communication of application modules 36 with application processors 14, one or more input devices 44, one or more output devices 46, UID 12, one or more sensors 10, motion module 6, and sensor control module 8. Each of application modules 36 may include program instructions and/or data that are executable by mobile computing device 4 (e.g., by one or more application processors 14).

UIM 38 may cause UID 12 to output a graphical user interface (e.g., graphical user interfaces 20, 24) for display, which may enable a user of mobile computing device 4 to view output and/or provide input at UID 12. UIM 38 and UID 12 may receive one or more indications of input from a user as the user interacts with the graphical user interface, at different times and when the user and mobile computing device 4 are at different locations. UIM 38 and UID 12 may interpret inputs detected at UID 12 (e.g., as a user provides one or more gestures at one or more locations of UID 12 at which the graphical user interface is displayed) and may relay information about the inputs detected at UID 12 to one or more associated platforms, operating systems, applications, and/or services executing at mobile computing device 4, to cause mobile computing device 4 to perform functions.

UIM 38 may receive information and instructions from one or more associated platforms, operating systems, applications, and/or services executing at mobile computing device 4 (e.g., application modules 36) for generating a graphical user interface. In addition, UIM 38 may act as an intermediary between the one or more associated platforms, operating systems, applications, and/or services executing at mobile computing device 4 and various output devices of mobile computing device 4 (e.g., speakers, LED indicators, audio or electrostatic haptic output device, etc.) to produce output (e.g., a graphic, a flash of light, a sound, a haptic response, etc.) with mobile computing device 4.

Battery 48 may provide power to one or more components of mobile computing device 4. Examples of battery 48 may include, but are not necessarily limited to, batteries having zinc-carbon, lead-acid, nickel cadmium (NiCd), nickel metal hydride (NiMH), lithium ion (Li-ion), and/or lithium ion polymer (Li-ion polymer) chemistries. Battery 48 may have a limited capacity (e.g., 1000-3000 mAh).

Modules 28, 32, 36, and 38 may perform operations described herein using software, hardware, firmware, or any combination of hardware, software, and firmware residing in and executing on mobile computing device 4. Computing device 4 may execute modules 28, 32, 36, and 38 with multiple processors. Computing device 4 may execute any of modules 28, 32, 36, and 38 as or within a virtual machine executing on underlying hardware. Modules 28, 32, 36, and 38 may be implemented in various ways. For example, any of modules 28, 32, 36, and 38 may be implemented as a downloadable or pre-installed application or "app." In another example, any of modules 28, 32, 36, and 38 may be implemented as part of an operating system of mobile computing device 4.

Due to the limited capacity, the period of time for which mobile computing device 4 may operate with power provided by battery 48 may be based on the amount of power consumed by mobile computing device 4. As such, in order to increase the period of time for which mobile computing device 4 may operate with power provided by battery 48, it may be desirable to reduce the amount of power consumed by mobile computing device 4. As it may be undesirable to reduce performance while a user is interacting (i.e., using) mobile computing device 4, it may be desirable to reduce the amount of power consumed by mobile computing device 4 while not in use by the user.

In accordance with one or more techniques of this disclosure, rather than continuously determining a current activity of a user based on analysis of motion data for various periods of time, mobile computing device 4 may activate a user activity determination process responsive to a determined change in the angle of mobile computing device 4 by motion module 6 and/or SCM 8. That is, mobile computing device 4 may perform the user activity recognition process in response to determining that mobile computing device 4 has tilted. For instance, mobile computing device 4 may determine that mobile computing device 4 has tilted in response to motion data indicating that a change in the angle of mobile computing device 4 relative to gravity satisfies a threshold amount of change, such as a change of 35 degrees.

As one example, application processors 14 may determine, while in a first power mode and based on first motion data generated by motion sensor 24, a first activity of a user associated with mobile computing device 4, where the first motion data indicating movement of the mobile computing device during a first time period (e.g., 1 second, 3 seconds, 10 seconds, etc.). While application processors determine a first activity of the user, mobile computing device 4 may be in a first orientation. For example, mobile computing device 4 may be in a substantially horizontal orientation (i.e., as illustrated by first orientation 18 of FIG. 1), such as lying on a table or desk. As another example, mobile computing device 4 may be on a user's person (e.g., in a pocket of a user and/or in a user's hand which may be at the user's side), in which case mobile computing device 4 may be in a horizontal orientation, a vertical orientation, or some other orientation.

After determining the current activity of the user, mobile computing device 4 may be in a low-power state in which one or more components of mobile computing device 4 may be off, deactivated, sleeping, have limited functionality, etc. For instance, at the first time, a display of UID 12 may be deactivated, one or more of sensors 10 may be off, and SCM 8 and application processors 14 may be in a low power or "sleep" state. In this way, mobile computing device 4 may consume a reduced amount of power in the low-power state when compared to a normal operating state. That is, application processors 14 may transition from operating in the first power mode to operating in a second power mode, wherein the processor consumes less power while operating in the second power mode than while operating in the first power mode.

In any case, the user may move mobile computing device 4 from a first to a second orientation (e.g., by picking up the device, standing up with the device in the user's pocket, etc.). Prior to mobile computing device being tilted, mobile computing device 4 may be in a static operating state. In the static operating state, motion sensor 24 may provide motion data corresponding to the movement of mobile computing device 4 to tilt module 28. Based on the motion data received from sensor 24, tilt module 28 may determine that, at the first time, mobile computing device 4 has tilted. For instance, tilt module 28 may determine that mobile computing device 4 has tilted if the motion data received from motion sensor 24 indicates that the change in the angle of mobile computing device 4 relative to gravity satisfies a threshold amount of change. In some examples, tilt module 28 may determine that mobile computing device 4 has moved from a first orientation to a second orientation. That is, while application processors 14 are operating in the second power mode, tilt module 28 of motion module 6 may determine, based on second motion data generated by motion sensor 24, that a change in an angle of the mobile computing device relative to gravity satisfies a threshold amount of change.

In some examples, tilt module 28 may analyze one or more axes of motion data as a group. For instance, tilt module 28 may determine that a derivative of a combination of two or more axes acceleration data is greater than a threshold. In any case, responsive to determining that mobile computing device 4 has tilted, tilt module 28 may output a signal (e.g., an interrupt signal) to SCM 8. In some examples, responsive to determining that mobile computing device 4 has tilted, mobile computing device 4 may transition from the static operational state to an "activity detection" operational state. That is, responsive to determining that the change in the angle satisfies the threshold amount of change, applications processors 14 may transition from operating in the second power mode to operating in the first power mode. In some examples, mobile computing device 4 may transition from the static operational state to the activity detection operational state when mobile computing device 4 has tilted.

In the activity detection operation state, mobile computing device 4 may determine a current activity of a user of mobile computing device 4. For example application processors 14 may determine, based on second motion data generated by motion sensor 24 during a second time period, a second activity of the user of mobile computing device 4. To detect an activity transition, application processors 14 may determine whether the second activity (i.e., the user activity determined after the tilt event) is different from the first activity (e.g., the user activity determined prior to the tilt event).

Responsive to determining that the second activity is different from the first activity, mobile computing device 4 may perform an action. The action may include storing a current location of mobile computing device 4 (e.g., based on sensor data received from a global positioning system sensor), outputting information about the first or second activity, or any other action. Mobile computing device 4 may determine the particular action based on the first activity, the second activity, the determination that the second activity is different from the first activity, or any combination thereof. For example, if the first activity is walking and the second activity is running, mobile computing device 4 may store a current location of mobile computing device 4 as a start location of a run. As another example, if the first activity is riding in a vehicle (e.g., driving the vehicle, passenging in the vehicle, etc.) and the second activity is walking, mobile computing device 4 may store a current location of mobile computing device 4 as an indication of a location at which the vehicle is parked.

In some examples, mobile computing device 4 may detect additional tilt events. For example, motion module 6 may determine, based on third motion data generated by motion sensor 24, that a second change in the angle of mobile computing device 4 relative to gravity satisfies the threshold amount of change and application processors 14 may determine, based on fourth motion data generated by motion sensor 24 during a third time period, a third activity of a user of the mobile computing device. Responsive to determining that the third activity is different from the second activity, mobile computing device 4 (e.g., application processors 14) may output, for display, a duration of time that elapsed between determining that the second activity was different from the first activity and determining that the third activity was different from the second activity.

Mobile computing device 4 may also be configured to use the detected activity transitions to provide additional details about the particular detected user activities. For example, subsequent to determining that a user is running, biking, walking, driving, or engaged in some other activity in which the user is moving and prior to determining that a change in the angle of mobile computing device 4 relative to gravity satisfies the threshold amount of change (i.e., that mobile computing device 4 tilted after determining the current user activity), mobile computing device 4 may store a series of locations of mobile computing device 4 during the current user activity such that the series of locations indicates a route of the user while the user was engaged in the current user activity. Responsive to determining that the second change in the angle of the mobile computing device relative to gravity satisfies the threshold amount of change (e.g., that the user likely changed activities), mobile computing device 4 may output an indication of the route.

Figure 3:
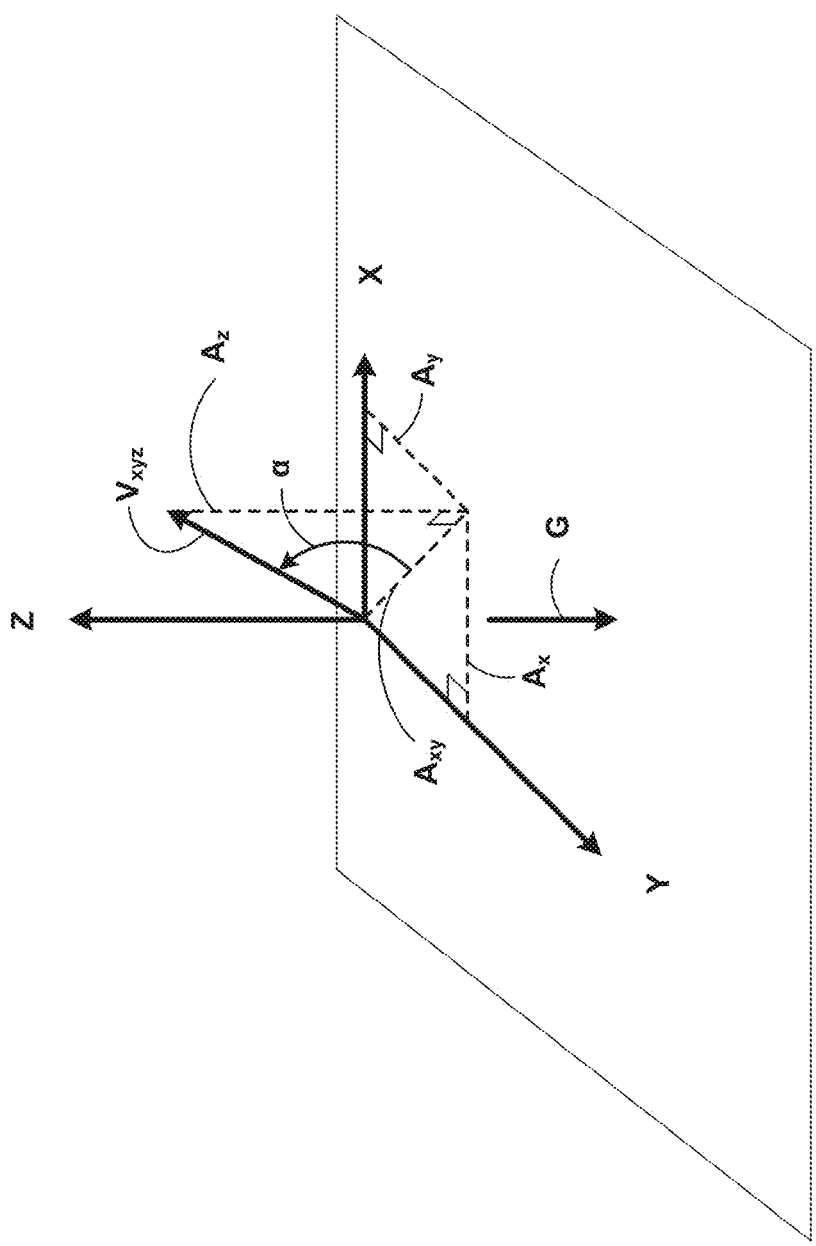
FIG. 3 illustrates an example orientation vector of a mobile device detected by a motion sensor, in accordance with one or more techniques of the present disclosure.

FIG. 3 illustrates an example orientation vector of a mobile device detected by a motion sensor, in accordance with one or more techniques of the present disclosure. As illustrated by FIG. 3, $V_{XYZ}$ may correspond to a vector, which represents the orientation of a device, such as $V_{CD}$ of mobile computing device 4 as illustrated in FIG. 1, in three dimensions.

The orientation of mobile computing device 4, and, in particular, the vector, $V_{xyz}$ may be defined by the magnitudes of the vector in the X, Y, and Z directions $A_x$, $A_y$, and $A_z$, respectively, as well as the angles between the vector and each of the X, Y, and Z axes (not shown in FIG. 3). In some examples, one or more processors of mobile computing device 4 may operate according to one or more techniques that approximate the orientation of mobile computing device 4 as one of horizontal or vertical based on the angle, α, between the orientation vector, $V_{xyz}$, and the projection of the vector onto the horizontal X-Y plane.

For example, one or more of processors 26 and/or processors 30 may receive the magnitudes $A_x$, $A_y$, $A_z$ of vector, $V_{xyz}$ in the X, Y, Z directions from a motion sensor, such as motion sensor 24, respectively in the example of FIG. 3. One or more of processors 26 and/or processors 30 may then calculate the magnitude, $A_{xy}$, of the projection of vector, $V_{xyz}$ in the X-Y plane according to the following formula.

$$A_{xy} = \sqrt{A_x^2 + A_y^2} \qquad (1)$$

One or more of processors 26 and/or processors 30 may then calculate the angle, α, between the orientation vector, $V_{xyz}$, and the projection of the vector onto the horizontal X-Y plane as a function of the arc tangent of the magnitude, $A_z$, of the vertical component of the orientation vector, $V_{xyz}$ and the magnitude, $A_{xy}$, of the projection of the vector in the X-Y plane. For example, one or more of processors 26 and/or processors 30 may calculate the angle, α, according to the following formula.

$$\alpha = \arctan\left(\frac{A_z}{A_{xy}}\right) \qquad (2)$$

In one example, one or more of processors 26 and/or processors 30 may approximate the orientation of mobile computing device 4 as vertical when the angle, α, between the orientation vector, $V_{xyz}$, and the projection of the vector onto the horizontal X-Y plane is greater than a threshold. In some examples, the threshold may be 35 degrees. In some examples, the threshold may be 50 degrees.

In accordance with or more techniques of this disclosure, one or more of processors 26 may determine, based on motion data measured by motion sensor 24, that mobile computing device 4 has moved from a first orientation to a second, different orientation. For instance, one or more of processors 26 may determine the magnitude, $A_{xy}$, of the projection of vector, $V_{xyz}$ in accordance with formula (1), above, at a first time (resulting in $A_{xy1}$) and at a second time ($A_{xy2}$). In some examples, if the difference between $A_{xy1}$ and $A_{xy2}$ is greater than a threshold, one or more of processors 26 may determine that mobile computing device 4 has tilted.

Figure 4:
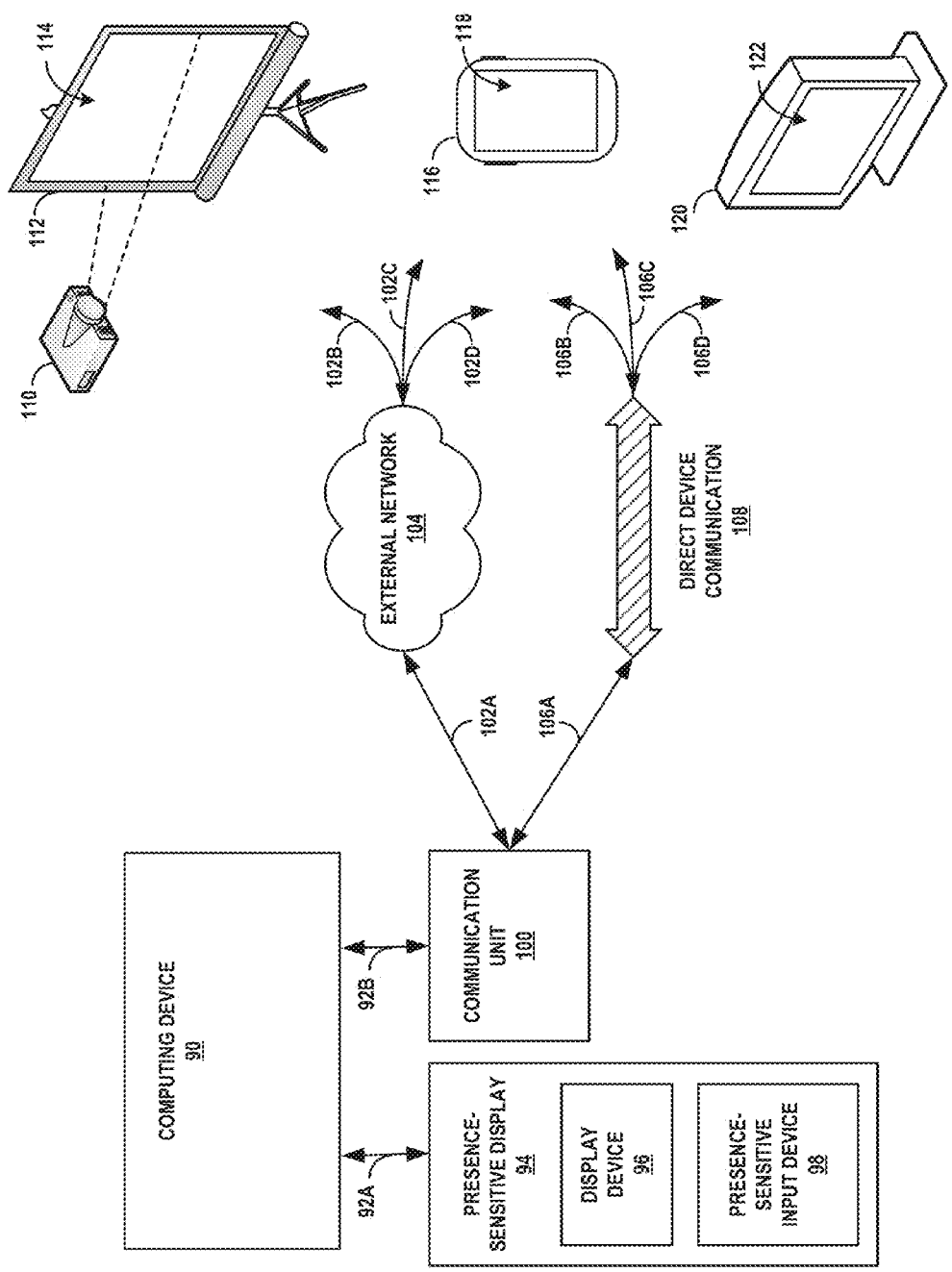
FIG. 4 is a block diagram illustrating an example computing device that outputs graphical content for display at a remote device, in accordance with one or more techniques of the present disclosure.

FIG. 4 is a block diagram illustrating an example computing device that outputs graphical content for display at a remote device, in accordance with one or more techniques of the present disclosure. Graphical content, generally, may include any visual information that may be output for display, such as text, images, a group of moving images, etc. The example shown in FIG. 4 includes a computing device 90, presence-sensitive display 94, communication unit 100, projector 110, projector screen 112, mobile device 116, and visual display device 120. Although shown for purposes of example in FIGS. 1 and 2 as stand-alone mobile computing device 4, a computing device, such as computing device 90 may, generally, be any component or system that includes a processor or other suitable computing environment for executing software instructions and, for example, need not include a presence-sensitive display.

As shown in the example of FIG. 4, computing device 90 may be a processor that includes functionality as described with respect to processor 40 in FIG. 2. In such examples, computing device 90 may be operatively coupled to presence-sensitive display 94 by a communication channel 92A, which may be a system bus or other suitable connection. Computing device 90 may also be operatively coupled to communication unit 100, further described below, by a communication channel 92B, which may also be a system bus or other suitable connection. Although shown separately as an example in FIG. 4, computing device 90 may be operatively coupled to presence-sensitive display 94 and communication unit 100 by any number of one or more communication channels.

In other examples, such as illustrated previously by mobile computing device 4 in FIGS. 1-2, a computing device may refer to a portable or mobile device such as mobile phones (including smart phones), wearable computing devices (including smart watches) laptop computers, etc.

Presence-sensitive display 94, like UID 12 of FIG. 1, may include display device 96 and presence-sensitive input device 98. Display device 96 may, for example, receive data from computing device 90 and display the graphical content. In some examples, presence-sensitive input device 98 may determine one or more user inputs (e.g., continuous gestures, multi-touch gestures, single-touch gestures, etc.) at presence-sensitive display 94 using capacitive, inductive, and/or optical recognition techniques and send indications of such user input to computing device 90 using communication channel 92A. In some examples, presence-sensitive input device 98 may be physically positioned on top of display device 96 such that, when a user positions an input unit over a graphical element displayed by display device 96, the location at which presence-sensitive input device 98 corresponds to the location of display device 96 at which the graphical element is displayed. In other examples, presence-sensitive input device 98 may be positioned physically apart from display device 96, and locations of presence-sensitive input device 98 may correspond to locations of display device 96, such that input can be made at presence-sensitive input device 98 for interacting with graphical elements displayed at corresponding locations of display device 96.

As shown in FIG. 4, computing device 90 may also include and/or be operatively coupled with communication unit 100. Communication unit 100 may include functionality of communication unit 42 as described in FIG. 2. Examples of communication unit 100 may include a network interface card, an Ethernet card, an optical transceiver, a radio frequency transceiver, or any other type of device that can send and receive information. Other examples of such communication units may include Bluetooth, 3G, and Wi-Fi radios, Universal Serial Bus (USB) interfaces, etc. Computing device 90 may also include and/or be operatively coupled with one or more other devices, e.g., input devices, output devices, memory, storage devices, etc. that are not shown in FIG. 4 for purposes of brevity and illustration.

FIG. 4 also illustrates a projector 110 and projector screen 112. Other such examples of projection devices may include electronic whiteboards, holographic display devices, and any other suitable devices for displaying graphical content. Projector 110 and projector screen 112 may include one or more communication units that enable the respective devices to communicate with computing device 90. In some examples, the one or more communication units may enable communication between projector 110 and projector screen 112. Projector 110 may receive data from computing device 90 that includes graphical content. Projector 110, in response to receiving the data, may project the graphical content onto projector screen 112. In some examples, projector 110 may determine one or more user inputs (e.g., continuous gestures, multi-touch gestures, single-touch gestures, etc.) at projector screen using optical recognition or other suitable techniques and send indications of such user input using one or more communication units to computing device 90. In such examples, projector screen 112 may be unnecessary, and projector 110 may project graphical content on any suitable medium and detect one or more user inputs using optical recognition or other such suitable techniques.

Projector screen 112, in some examples, may include a presence-sensitive display 114. Presence-sensitive display 114 may include a subset of functionality or all of the functionality of UID 10 as described in this disclosure. In some examples, presence-sensitive display 94 may include additional functionality. Projector screen 112 (e.g., an electronic whiteboard) may receive data from computing device 90 and display the graphical content. In some examples, presence-sensitive display 114 may determine one or more user inputs (e.g., continuous gestures, multi-touch gestures, single-touch gestures, etc.) at projector screen 112 using capacitive, inductive, and/or optical recognition techniques and send indications of such user input using one or more communication units to computing device 80.

FIG. 4 also illustrates mobile device 116 and visual display device 120. Mobile device 116 and visual display device 120 may each include computing and connectivity capabilities. Examples of mobile device 116 may include e-reader devices, convertible notebook devices, hybrid slate devices, wearable computing devices, etc. Examples of visual display device 120 may include other semi-stationary devices such as televisions, computer monitors, etc. As shown in FIG. 4, mobile device 116 may include a presence-sensitive display 118. Visual display device 120 may include a presence-sensitive display 122. Presence-sensitive displays 118, 122 may include a subset of functionality or all of the functionality of UID 10 as described in this disclosure. In some examples, presence-sensitive displays 118, 122 may include additional functionality. In any case, presence-sensitive display 122, for example, may receive data from computing device 90 and display the graphical content. In some examples, presence-sensitive display 122 may determine one or more user inputs (e.g., continuous gestures, multi-touch gestures, single-touch gestures, etc.) at projector screen using capacitive, inductive, and/or optical recognition techniques and send indications of such user input using one or more communication units to computing device 90.

As described above, in some examples, computing device 90 may output graphical content for display at presence-sensitive display 94 that is coupled to computing device 90 by a system bus or other suitable communication channel. Computing device 90 may also output graphical content for display at one or more remote devices, such as projector 110, projector screen 112, mobile device 116, and visual display device 120. For instance, computing device 90 may execute one or more instructions to generate and/or modify graphical content in accordance with techniques of the present disclosure. Computing device 90 may output the data that includes the graphical content to a communication unit of computing device 90, such as communication unit 100. Communication unit 100 may send the data to one or more of the remote devices, such as projector 110, projector screen 112, mobile device 116, and/or visual display device 120. In this way, computing device 90 may output the graphical content for display at one or more of the remote devices. In some examples, one or more of the remote devices may output the graphical content at a presence-sensitive display that is included in and/or operatively coupled to the respective remote devices.

In some examples, computing device 90 may not output graphical content at presence-sensitive display 94 that is operatively coupled to computing device 90. In other examples, computing device 90 may output graphical content for display at both a presence-sensitive display 94 that is coupled to computing device 90 by communication channel 92A, and at one or more remote devices. In such examples, the graphical content may be displayed substantially contemporaneously at each respective device. For instance, some delay may be introduced by the communication latency to send the data that includes the graphical content to the remote device. In some examples, graphical content generated by computing device 90 and output for display at presence-sensitive display 94 may be different than graphical content display output for display at one or more remote devices.

Computing device 90 may send and receive data using any suitable communication techniques. For example, computing device 90 may be operatively coupled to external network 104 using network link 102A. Each of the remote devices illustrated in FIG. 4 may be operatively coupled to network external network 104 by one of respective network links 102B, 102C, and 102D. External network 104 may include network hubs, network switches, network routers, etc., that are operatively inter-coupled thereby providing for the exchange of information between computing device 90 and the remote devices illustrated in FIG. 4. In some examples, network links 102A-102D may be Ethernet, ATM or other network connections. Such connections may be wireless and/or wired connections.

In some examples, computing device 90 may be operatively coupled to one or more of the remote devices included in FIG. 4 using direct device communication 108. Direct device communication 108 may include communications through which computing device 90 sends and receives data directly with a remote device, using wired or wireless communication. That is, in some examples of direct device communication 108, data sent by computing device 90 may not be forwarded by one or more additional devices before being received at the remote device, and vice-versa. Examples of direct device communication 108 may include Bluetooth, Near-Field Communication, Universal Serial Bus, Wi-Fi, infrared, etc. One or more of the remote devices illustrated in FIG. 4 may be operatively coupled with computing device 90 by communication links 106A-106D. In some examples, communication links 106A-106D may be connections using Bluetooth, Near-Field Communication, Universal Serial Bus, infrared, etc. Such connections may be wireless and/or wired connections.

In accordance with techniques of the disclosure, computing device 90 may be operatively coupled to visual display device 120 using external network 104. A first motion module of computing device 90 may determine, based on motion data measured by a motion sensor, that computing device 90 has tilted. Responsive to determining that computing device 90 has tilted, computing device 90 may determine a current activity of a user of computing device 90 and may output, for display, information associated with a prior activity of the user and/or the current activity of the user. For example, computing device 90 output information associated with a user activity at display device 96 of presence-sensitive display 94, projector 110, presence-sensitive display 118 of mobile device 116, and/or presence-sensitive display 122 of visual display device 120.

Figure 5:
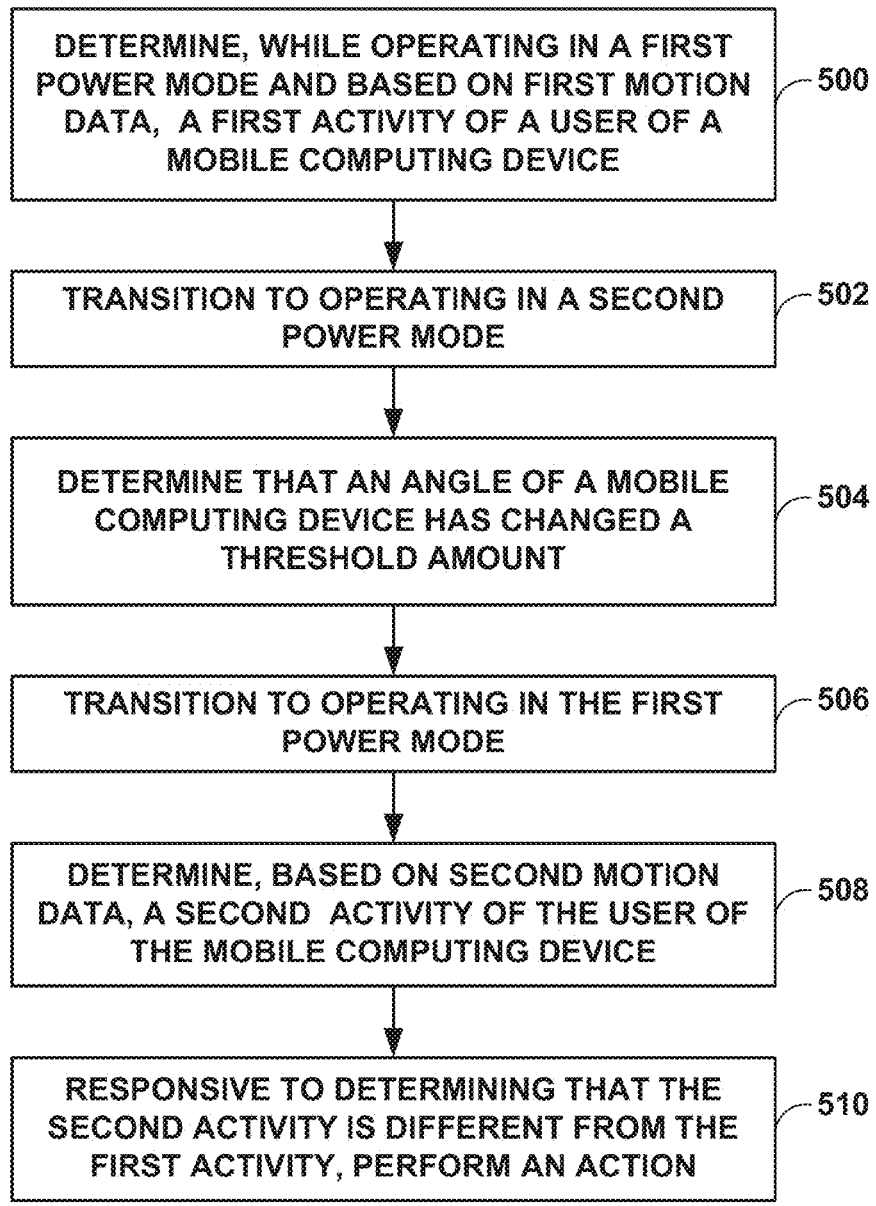
FIG. 5 is a flow diagram illustrating example operations of a computing device that detects activity transitions, in accordance with one or more techniques of the present disclosure.

FIG. 5 is a flow diagram illustrating example operations of a computing device to activate a display responsive to determining that a user is attempting to use the device, in accordance with one or more techniques of the present disclosure. The techniques of FIG. 5 may be performed by one or more processors of a computing device, such as mobile computing device 4 illustrated in FIG. 1 and FIG. 2. For purposes of illustration, the techniques of FIG. 5 are described within the context of mobile computing device 4 of FIG. 1 and FIG. 2, although computing devices having configurations different than that of mobile computing device 4 may perform the techniques of FIG. 5.

In accordance with one or more techniques of the disclosure, application processors 14 of mobile computing device 4 may analyze motion data generated by motion sensor 24 to determine a first activity of a user associated with mobile computing device 4 (500). Typically, application processors 14 operate in a first power mode while determining the first activity. The motion data generated by motion sensors 24 indicates movement of mobile computing device 4 during a first time period. Application processors 14 may transition from operating in the first power mode to operating in a second power mode (502). Application processors may perform this transition after determining the first activity of the user. In general, application processors 14 consume less power while operating in the second power mode than while operating in the first power mode.

While application processors 14 are operating in the second power mode, motion module 6 of mobile computing device 4 may determine, based on second motion data generated by motion sensor 24, that a change in an angle of mobile computing device 4 relative to gravity satisfies a threshold amount of change (504). For example, the second motion data may indicate the change in the angle of mobile computing device 4 relative to gravity exceeds 35 degrees. When the change in the angle of mobile computing device 4 satisfies the threshold, motion module 6 may determine that mobile computing device has tilted. Responsive to determining that the change in the angle satisfies the threshold amount of change, motion module 6 may cause application processors 14 to transition from operating in the second power mode to operating in the first power mode (506).

Application processors 14 may determine, based on second motion data generated by motion sensor 24 during a second time period, a second activity of the user of mobile computing device 4 (508). Responsive to determining that the second activity is different from the first activity, mobile computing device 4 may perform an action determined based on the determining that the second activity is different from the first activity (510).

Example 1

A method comprising: determining, by a processor of a mobile computing device operating in a first power mode and based on first motion data generated by a motion sensor of the mobile computing device, a first activity of a user associated with the mobile computing device, the first motion data indicating movement of the mobile computing device during a first time period; transitioning, by processor, from operating in the first power mode to operating in a second power mode, wherein the processor consumes less power while operating in the second power mode than while operating in the first power mode; while the processor is operating in the second power mode, determining, by a motion module of the mobile computing device and based on second motion data generated by the motion sensor, that a change in an angle of the mobile computing device relative to gravity satisfies a threshold amount of change; responsive to determining that the change in the angle satisfies the threshold amount of change, transitioning, by processor, from operating in the second power mode to operating in the first power mode; determining, by the processor and based on second motion data generated by the motion sensor during a second time period, a second activity of the user of the mobile computing device; and, responsive to determining that the second activity is different from the first activity, performing, by the mobile computing device, an action determined based on the determining that the second activity is different from the first activity.

Example 2

The method of example 1, wherein the performing the action comprises storing an indication of a current location of the mobile computing device.

Example 3

The method of any combination of examples 1-2, wherein the change in the angle of the mobile computing device relative to gravity is a second change in the angle of the mobile computing device, the method further comprising: prior to determining, by the processor, the first activity of the user, determining, by the motion module based on third motion data generated by the motion sensor, that a first change in an angle of the mobile computing device relative to gravity satisfies the threshold amount of change, wherein performing the action comprises: determining, by the processor, a plurality of previously determined activities, wherein each previously determined activity was determined during a time period occurring between the determining that the first change in an angle of the mobile computing device relative to gravity satisfies the threshold amount of change and determining that the second change in an angle of the mobile computing device relative to gravity satisfies the threshold amount of change; and, responsive to determining, by the processor, that at least one previously determined activity from the plurality of previously determined activities is incorrect, correcting the at least one previously determined activity.

Example 4

The method of example 3, wherein correcting the at least one previously determined activity comprises one or more of: removing the at least one previously determined activity from the plurality of previously determined activity; and changing the at least one previously determined activity to correspond to an activity of a majority of the plurality of previously determined activities.

Example 5

The method of any combination of examples 1-4, wherein the change in the angle of the mobile computing device is a first change in the angle of the mobile computing device, the method further comprising: determining, by the motion module and based on third motion data generated by the motion sensor, that a second change in the angle of the mobile computing device relative to gravity satisfies the threshold amount of change; determining, by the processor and based on fourth motion data generated by the motion sensor during a third time period, a third activity of a user of the mobile computing device; and, responsive to determining that the third activity is different from the second activity, outputting, by the mobile computing device and for display, a duration of time that elapsed between determining that the second activity was different from the first activity and determining that the third activity was different from the second activity.

Example 6

The method of example 5, further comprising: prior to determining that the second change in the angle of the mobile computing device relative to gravity satisfies the threshold amount of change, storing a series of locations of the mobile computing device indicating a route of the user; and, responsive to determining that the second change in the angle of the mobile computing device relative to gravity satisfies the threshold amount of change, outputting, by the mobile computing device and for display, an indication of the route.

Example 7

The method of example 5, further comprising: responsive to determining that the third activity is different from the second activity, outputting, by the mobile computing device and for display, an indication of the second activity.

Example 8

The method of any combination of examples 1-7, wherein performing the action comprises determining a current location of the mobile computing device, wherein the second activity is running or bicycling, and wherein the current location corresponds to the start of a run or bicycle ride.

Example 9

The method of any combination of examples 1-7, wherein performing the action comprises determining a current location of the mobile computing device, wherein the first activity is riding in a vehicle, wherein the second activity is walking, and wherein the indication of the current location of the mobile computing device indicates a location at which the vehicle is parked.

Example 10

The method of any combination of examples 1-9, wherein the motion module includes the motion sensor and a first processor, wherein the processor is an application processor, and wherein the first processor and the application processor are different processors.

Example 11

The method of any combination of examples 1-10, wherein the motion sensor is an accelerometer.

Example 12

A mobile computing device comprising: one or more processors; a motion sensor; and a motion module, wherein at least one processor of the one or more processors determines, while the at least one processor is operating in a first power mode and based on first motion data generated by the motion sensor, a first activity of a user associated with the mobile computing device, the first motion data indicating movement of the mobile computing device during a first time period, and transitions the mobile computing device from operating in the first power mode to operating in a second power mode, wherein the one or more processors consume less power while operating in the second power mode than while operating in the first power mode, wherein the motion module determines, while the mobile computing device is operating in the second power mode and based on second motion data generated by the motion sensor, that a change in an angle of the mobile computing device relative to gravity satisfies a threshold amount of change, and wherein the at least one processor of the one or more processors, responsive to the motion module determining that the change in the angle satisfies the threshold amount of change, transitions the mobile computing device from operating in the second power mode to operating in the first power mode, determines, based on second motion data generated by the motion sensor during a second time period, a second activity of the user of the mobile computing device, and, responsive to determining that the second activity is different from the first activity, performs an action determined based on the determining that the second activity is different from the first activity.

Example 13

The mobile computing device of example 12, wherein the action comprises storing an indication of a current location of the mobile computing device.

Example 14

The mobile computing device of any combination of examples 12-13, wherein the change in the angle of the mobile computing device relative to gravity is a second change in the angle of the mobile computing device, and wherein the motion module, prior to the at least one processor determining the first activity of the user, determines, based on third motion data generated by the motion sensor, that a first change in an angle of the mobile computing device relative to gravity satisfies the threshold amount of change, wherein the at least one processors performs the action by at least: determining, by the processor, a plurality of previously determined activities, wherein each previously determined activity was determined during a time period occurring between the determining that the first change in an angle of the mobile computing device relative to gravity satisfies the threshold amount of change and determining that the second change in an angle of the mobile computing device relative to gravity satisfies the threshold amount of change; and, responsive to determining, by the processor, that at least one previously determined activity from the plurality of previously determined activities is incorrect, correcting the at least one previously determined activity.

Example 15

The mobile computing device of example 14, wherein the at least one processor corrects the at least one previously determined activity by at least performing one or more of: removing the at least one previously determined activity from the plurality of previously determined activity; and changing the at least one previously determined activity to correspond to an activity of a majority of the plurality of previously determined activities.

Example 16

The computing device of any combination of examples 12-15, wherein the change in the angle of the mobile computing device is a first change in the angle of the mobile computing device, wherein the motion module determines, based on third motion data generated by the motion sensor, that a second change in the angle of the mobile computing device relative to gravity satisfies the threshold amount of change, and wherein the at least one of the one or more processors determines, based on fourth motion data generated by the motion sensor during a third time period, a third activity of a user of the mobile computing device, and, responsive to determining that the third activity is different from the second activity, outputs, for display, a duration of time that elapsed between determining that the second activity was different from the first activity and determining that the third activity was different from the second activity.

Example 17

The mobile computing device of example 16, wherein the at least one of the one or more processors, prior to the motion module determining that the second change in the angle of the mobile computing device relative to gravity satisfies the threshold amount of change, stores a series of locations of the mobile computing device indicating a route of the user, and, responsive to determining that the second change in the angle of the mobile computing device relative to gravity satisfies the threshold amount of change, outputs, for display, an indication of the route.

Example 18

The mobile computing device of example 16, wherein the at least one of the one or more processors, responsive to determining that the third activity is different from the second activity, outputs, for display, an indication of the second activity.

Example 19

The computing device of any combination of examples 12-18, wherein performing the action comprises determining a current location of the mobile computing device, wherein the second activity is running or bicycling, and wherein the current location corresponds to the start of a run or bicycle ride.

Example 20

The mobile computing device of any combination of examples 12-19, wherein the first activity is riding in a vehicle, wherein the second activity is walking, and wherein the indication of the current location of the mobile computing device indicates a location at which the vehicle is parked.

Example 21

The computing device of any combination of examples 12-20, wherein the motion module includes the motion sensor and a first processor, wherein the processor is an application processor, and wherein the first processor and the application processor are different processors.

Example 22

The computing device of any combination of examples 12-21, wherein the motion sensor is an accelerometer.

Example 23

A non-transitory computer-readable storage encoded with instructions that, when executed, cause at least one of a plurality of processors of a mobile computing device to: determine, while the at least one processor is operating in a first power mode and based on first motion data generated by a motion sensor of the mobile computing device, a first activity of a user associated with the mobile computing device, the first motion data indicating movement of the mobile computing device during a first time period; transition, by the at least one processor, from operating in the first power mode to operating in a second power mode, wherein the at least one processor consumes less power while operating in the second power mode than while operating in the first power mode; while the at least one processor is operating in the second power mode, determine, by a motion module and based on second motion data generated by the motion sensor, that a change in an angle of the mobile computing device relative to gravity satisfies a threshold amount of change; responsive to determining that the change in the angle satisfies the threshold amount of change, transition, by the at least one processor, from operating in the second power mode to operating in the first power mode; determine, based on second motion data generated by the motion sensor during a second time period, a second activity of the user of the mobile computing device; and responsive to determining that the second activity is different from the first activity, perform an action determined based on the determining that the second activity is different from the first activity.

Example 24

A non-transitory computer-readable storage medium encoded with instructions that, when executed, cause at least one of a plurality of processors of a mobile computing device to perform any combination of the techniques of examples 1-11.

Example 25

A device comprising means for performing any combination of the techniques of examples 1-12.

Example 26

A system comprising means for performing any combination of the techniques of examples 1-12.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described. These and other examples are within the scope of the following claims.

The invention claimed is:

1. A method comprising:
   determining, by a processor of a mobile computing device operating in a first power mode and based on first motion data generated by a motion sensor of the mobile computing device, a first activity of a user associated with the mobile computing device, the first motion data indicating movement of the mobile computing device during a first time period;
   transitioning, by the processor, from operating in the first power mode to operating in a second power mode, wherein the processor consumes less power while operating in the second power mode than while operating in the first power mode;
   while the processor is operating in the second power mode, determining, by a motion module of the mobile computing device and based on second motion data generated by the motion sensor, that a first change in an angle of the mobile computing device relative to gravity satisfies a threshold amount of change;
   responsive to determining that the first change in the angle satisfies the threshold amount of change, transitioning, by the processor, from operating in the second power mode to operating in the first power mode;

determining, by the processor and based on second motion data generated by the motion sensor during a second time period, a second activity of the user of the mobile computing device;

determining, by the motion module and based on third motion data generated by the motion sensor, that a second change in the angle of the mobile computing device relative to gravity satisfies the threshold amount of change;

determining, by the processor and based on fourth motion data generated by the motion sensor during a third time period, a third activity of a user of the mobile computing device; and responsive to determining that the third activity is different from the second activity, outputting, by the mobile computing device and for display, an indication of a duration of time that elapsed between determining that the second activity was different from the first activity and determining that the third activity was different from the second activity.

2. The method of claim 1, further comprising:
responsive to determining that the second activity is different from the first activity, storing an indication of a current location of the mobile computing device.

3. The method of claim 1, further comprising:
prior to determining, by the processor, the first activity of the user, determining, by the motion module based on fifth motion data generated by the motion sensor, that a previous change in an angle of the mobile computing device relative to gravity satisfies the threshold amount of change;

determining, by the processor, a plurality of previously determined activities, wherein each previously determined activity was determined during a time period occurring between the determining that the previous change in an angle of the mobile computing device relative to gravity satisfies the threshold amount of change and determining that the first change in an angle of the mobile computing device relative to gravity satisfies the threshold amount of change; and responsive to determining, by the processor, that at least one previously determined activity from the plurality of previously determined activities is incorrect, correcting the at least one previously determined activity.

4. The method of claim 3, wherein correcting the at least one previously determined activity comprises one or more of:
removing the at least one previously determined activity from the plurality of previously determined activity; and
changing the at least one previously determined activity to correspond to an activity of a majority of the plurality of previously determined activities.

5. The method of claim 1, further comprising:
prior to determining that the second change in the angle of the mobile computing device relative to gravity satisfies the threshold amount of change, storing a series of locations of the mobile computing device indicating a route of the user; and responsive to determining that the second change in the angle of the mobile computing device relative to gravity satisfies the threshold amount of change, outputting, by the mobile computing device and for display, an indication of the route.

6. The method of claim 1, further comprising:
responsive to determining that the third activity is different from the second activity, outputting, by the mobile computing device and for display, an indication of the second activity.

7. The method of claim 1, further comprising:
responsive to determining that the second activity is different from the first activity, determining a current location of the mobile computing device,
wherein the second activity is running or bicycling, and
wherein the current location corresponds to the start of a run or bicycle ride.

8. The method of claim 1, further comprising:
responsive to determining that the second activity is different from the first activity:
determining a current location of the mobile computing device; and
storing, by the mobile computing device, an indication of the current location,
wherein the first activity is riding in a vehicle,
wherein the second activity is walking, and
wherein the indication of the current location of the mobile computing device indicates a location at which the vehicle is parked.

9. The method of claim 1,
wherein the motion module includes the motion sensor and a first processor,
wherein the processor is an application processor, and
wherein the first processor and the application processor are different processors.

10. The method of claim 1, wherein the motion sensor is an accelerometer.

11. A mobile computing device comprising:
one or more processors;
a motion sensor; and
a motion module,
wherein at least one processor of the one or more processors determines, while the at least one processor is operating in a first power mode and based on first motion data generated by the motion sensor, a first activity of a user associated with the mobile computing device, the first motion data indicating movement of the mobile computing device during a first time period, and transitions the mobile computing device from operating in the first power mode to operating in a second power mode, wherein the one or more processors consume less power while operating in the second power mode than while operating in the first power mode, wherein the motion module determines, while the mobile computing device is operating in the second power mode and based on second motion data generated by the motion sensor, that a first change in an angle of the mobile computing device relative to gravity satisfies a threshold amount of change, wherein the at least one processor of the one or more processors, responsive to the motion module determining that the first change in the angle satisfies the threshold amount of change, transitions the mobile computing device from operating in the second power mode to operating in the first power mode, determines, based on second motion data generated by the motion sensor during a second time period, a second activity of the user of the mobile computing device, wherein the motion module determines, based on third motion data generated by the motion sensor, that a second change in the angle of the mobile computing device relative to gravity satisfies the threshold amount of change, and wherein the at least one processors of the one or more processors determines, based on fourth motion data generated by the motion sensor during a third time period, a third activity of a user of the mobile computing device, and, responsive to determining that the third activity is different from the second activity, outputs, for display, an indication of a duration of time that elapsed between determining that the second activity was different from the first activity and determining that the third activity was different from the second activity.

12. The mobile computing device of claim 11, further comprising:
wherein the at least one processors of the one or more processors stores an indication of a current location of the mobile computing device.

13. The mobile computing device of claim 11,
wherein the motion module, prior to the at least one processor determining the first activity of the user, determines, based on fifth motion data generated by the motion sensor, that a previous change in an angle of the mobile computing device relative to gravity satisfies the threshold amount of change, and
wherein the at least one processors determines a plurality of previously determined activities, wherein each previously determined activity was determined during a time period occurring between the determining that the first change in an angle of the mobile computing device relative to gravity satisfies the threshold amount of change and determining that the second change in an angle of the mobile computing device relative to gravity satisfies the threshold amount of change, and, responsive to determining that at least one previously determined activity from the plurality of previously determined activities is incorrect, corrects the at least one previously determined activity.

14. The mobile computing device of claim 11,
wherein the at least one processor corrects the at least one previously determined activity by at least performing one or more of:
removing the at least one previously determined activity from the plurality of previously determined activity; and
changing the at least one previously determined activity to correspond to an activity of a majority of the plurality of previously determined activities.

15. The mobile computing device of claim 11,
wherein the at least one of the one or more processors, prior to the motion module determining that the second change in the angle of the mobile computing device relative to gravity satisfies the threshold amount of change, stores a series of locations of the mobile computing device indicating a route of the user, and, responsive to determining that the second change in the angle of the mobile computing device relative to gravity satisfies the threshold amount of change, outputs, for display, an indication of the route.

16. The mobile computing device of claim 11, wherein the at least one of the one or more processors, responsive to determining that the third activity is different from the second activity, outputs, for display, an indication of the second activity.

17. The mobile computing device of claim 11, wherein the at least one of the one or more processors determines a current location of the mobile computing device, wherein the second activity is running or bicycling, and wherein the current location corresponds to the start of a run or bicycle ride.

18. The mobile computing device of claim 11,
wherein the at least one of the one or more processors determines a current location of the mobile computing device, and stores an indication of the current location,
wherein the first activity is riding in a vehicle,
wherein the second activity is walking, and
wherein the indication of the current location of the mobile computing device indicates a location at which the vehicle is parked.

19. The mobile computing device of claim 11,
wherein the motion module includes the motion sensor and a first processor,
wherein the processor is an application processor, and
wherein the first processor and the application processor are different processors.

20. The mobile computing device of claim 11, wherein the motion sensor is an accelerometer.

21. A non-transitory computer-readable storage medium encoded with instructions that, when executed, cause at least one of a plurality of processors of a mobile computing device to:
determine, while the at least one processor is operating in a first power mode and based on first motion data generated by a motion sensor of the mobile computing device, a first activity of a user associated with the mobile computing device, the first motion data indicating movement of the mobile computing device during a first time period;
transition, by the at least one processor, from operating in the first power mode to operating in a second power mode, wherein the at least one processor consumes less power while operating in the second power mode than while operating in the first power mode;
while the at least one processor is operating in the second power mode, determine, by a motion module and based on second motion data generated by the motion sensor, that a first change in an angle of the mobile computing device relative to gravity satisfies a threshold amount of change;
responsive to determining that the first change in the angle satisfies the threshold amount of change, transition, by the at least one processor, from operating in the second power mode to operating in the first power mode;
determine, based on second motion data generated by the motion sensor during a second time period, a second activity of the user of the mobile computing device;
determine, based on third motion data generated by the motion sensor, that a second change in the angle of the mobile computing device relative to gravity satisfies the threshold amount of change;
determine, based on fourth motion data generated by the motion sensor during a third time period, a third activity of a user of the mobile computing device; and
responsive to determining that the third activity is different from the second activity, output, for display, an indication of a duration of time that elapsed between determining that the second activity was different from the first activity and determining that the third activity was different from the second activity.

* * * * *